(12) United States Patent
Slater

(10) Patent No.: US 12,097,208 B2
(45) Date of Patent: Sep. 24, 2024

(54) METHOD FOR TREATING NASAL, SINONASAL, AND NASOPHARYNGEAL TISSUE INFECTION AND/OR INFLAMMATION

(71) Applicant: OTICARA, INC., Austin, TX (US)

(72) Inventor: Patrick Slater, Austin, TX (US)

(73) Assignee: Oticara, Inc., Austin, TX (US)

( * ) Notice: Subject to any disclaimer, the term of this patent is extended or adjusted under 35 U.S.C. 154(b) by 641 days.

(21) Appl. No.: 17/459,373

(22) Filed: Aug. 27, 2021

(65) Prior Publication Data

US 2021/0386760 A1 Dec. 16, 2021

Related U.S. Application Data

(63) Continuation of application No. PCT/US2020/020143, filed on Feb. 27, 2020.

(60) Provisional application No. 62/811,169, filed on Feb. 27, 2019.

(51) Int. Cl.
| A61K 31/573 | (2006.01) |
| A61K 9/00 | (2006.01) |
| A61K 9/06 | (2006.01) |
| A61K 31/137 | (2006.01) |
| A61K 31/27 | (2006.01) |
| A61K 31/4164 | (2006.01) |
| A61K 31/4174 | (2006.01) |
| A61K 31/4196 | (2006.01) |
| A61K 31/4418 | (2006.01) |
| A61K 31/496 | (2006.01) |
| A61K 31/506 | (2006.01) |
| A61K 31/7048 | (2006.01) |
| A61P 11/02 | (2006.01) |
| A61P 31/00 | (2006.01) |

(52) U.S. Cl.
CPC .......... *A61K 31/573* (2013.01); *A61K 9/0043* (2013.01); *A61K 9/06* (2013.01); *A61K 31/137* (2013.01); *A61K 31/27* (2013.01); *A61K 31/4164* (2013.01); *A61K 31/4174* (2013.01); *A61K 31/4196* (2013.01); *A61K 31/4418* (2013.01); *A61K 31/496* (2013.01); *A61K 31/506* (2013.01); *A61K 31/7048* (2013.01); *A61P 11/02* (2018.01); *A61P 31/00* (2018.01)

(58) Field of Classification Search
CPC ...... A61K 31/573; A61K 9/0043; A61K 9/06; A61K 31/137; A61K 31/27; A61K 31/4164; A61K 31/4174; A61K 31/4196; A61K 31/4418; A61K 31/496; A61K 31/506; A61K 31/7048; A61P 11/02
USPC ........................................................ 514/171
See application file for complete search history.

(56) References Cited

U.S. PATENT DOCUMENTS

| 6,656,491 | B1 | 12/2003 | Brosck et al. |
| 8,232,264 | B2 | 7/2012 | Gans et al. |
| 8,337,481 | B2 * | 12/2012 | Slater .................. A61K 31/351 |
| | | | 604/514 |
| 2005/0043706 | A1 | 2/2005 | Eaton et al. |
| 2005/0143393 | A1 | 6/2005 | Dean et al. |
| 2008/0261900 | A1 | 10/2008 | Tyle et al. |
| 2009/0253645 | A1 | 10/2009 | Ponikau |
| 2010/0129316 | A1 | 5/2010 | Levitt |
| 2010/0247694 | A1 | 9/2010 | Di Bartolomeo |
| 2014/0336463 | A1 | 11/2014 | Shikani |
| 2015/0174253 | A1 | 6/2015 | Sun et al. |

FOREIGN PATENT DOCUMENTS

| CN | 1427827 A | 7/2003 |
| CN | 101610753 A | 12/2009 |
| CN | 101437394 B | 10/2012 |
| CN | 102026623 B | 8/2013 |
| JP | 2008-512389 A | 4/2008 |
| JP | 2014-024768 A | 7/2014 |
| JP | 2016-094586 A | 5/2016 |
| WO | 2006029255 A2 | 3/2006 |

OTHER PUBLICATIONS

Dawson et al The Journal of Laryngology & Otology, 2018, 132, 143-149 (Year: 2018).*
Official Action mailed Sep. 29, 2023 for Canadian Patent Application No. 3,130,138.
Search Report mailed Apr. 16, 2024 for Chinese Patent Application No. 202080017059.5.
Official Action mailed Apr. 17, 2024 for Chinese Patent Application No. 202080017059.5.
Official Action mailed Mar. 5, 2024 for Japanese Patent Application No. 2021-550109.
Ohta, Yasushi, et al. Rinderon-V Ointment intranasal injection therapy for postoperative recurrent cases of eosinophilic sinusitis, Nippon Jibiinkoka Tokeibugeka Gakkai Kaiho, 2017, vol. 120, No. 4, pp. 635-637, 0-468.
Takayama et al., Kozo, et al. Pharmacological effects of flunisolide nasal ointments on experimental allergic rhinitis, Drug Delivery System, 2005, vol. 20, No. 2, pp. 138-144.
Betamethasone Dipropionate, Drugs in Japan—Ethical Drugs for the year 2009, supervised by the Japanese Pharmacopoeial Forum, 2009, pp. 2295-2296.
Betamethasone Valerate, Drugs in Japan—Ethical Drugs for the year 2009, supervised by the Japanese Pharmacopoeial Forum, 2009, pp. 2291-2293.
Extended European Search Report issued on Nov. 14, 2022 in European Patent Application No. 20763831.3.
Chien Y W et al: Intranasal Drug Delivery for Systemic Medications, Critical Reviews in Therapeutic Drug Carrier Systems, Begell House Publishing Inc, US vol. 4, No. 2, Jan. 1, 1987 (Jan. 1, 1987), pp. 67-194, XP001119352, ISSN: 0743-4863.

(Continued)

*Primary Examiner* — Yevgeny Valenrod
(74) *Attorney, Agent, or Firm* — Barnes & Thornburg LLP

(57) ABSTRACT

Compositions and methods are provided for treating diseases and conditions of the nasal, sinonasal and nasopharyngeal tissues.

18 Claims, 14 Drawing Sheets
(8 of 14 Drawing Sheet(s) Filed in Color)

(56) References Cited

OTHER PUBLICATIONS

Dawson B et al.: The effects of nasal lavage with betamethasone cream post-endoscopic sinus surgery: clinical trial, Journal of Laryngology and Otology, vol. 132,, No. 2, Feb. 12, 2018 (Feb. 12, 2018), pp. 143-149, XP055976453, GB ISSN: 0022-2151, DOI 10.1017/S0022215117001827 retrieved from internet URL: nttp://dx.doi.org/10.1017/S0022215117001827.

International Search Report and Written Opinion issued on May 19, 2020 in International Patent Application PCT/US2020/020143.

International Preliminary Report on Patentability issued on Aug. 25, 2021 in International Patent Application PCT/US2020/020143.

Haemophilus influenzae, Wikipedia, 2008 [retrieved from the internet on May 1, 2020 at <https://en.wikipedia.org/wiki/Haemophilus_influenzae >] para 1.

*Staphylococcus aureus*, Wikipedia, 2001, [retrieved from the Internet on May 1, 2020 at <https://en.wikipedia.org/wiki/Staphylococcus_aureus >] para 1.

\* cited by examiner

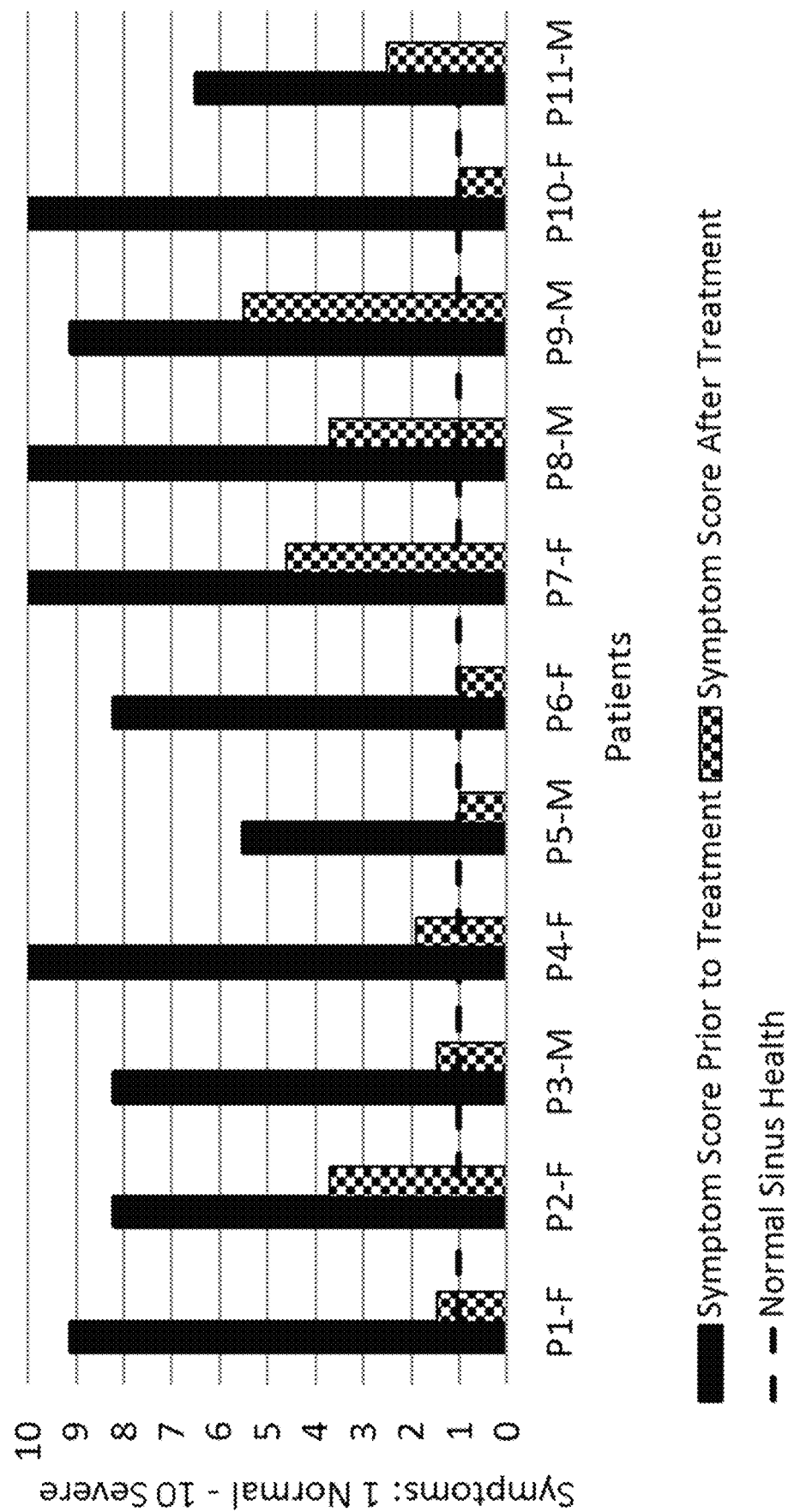

METHOD FOR TREATING NASAL, SINONASAL, AND NASOPHARYNGEAL TISSUE INFECTION AND/OR INFLAMMATION

CROSS-REFERENCE TO RELATED APPLICATIONS

The present application is a continuation of International Application No. PCT/US2020/020143, filed Feb. 27, 2020, the entire contents of which is hereby incorporated herein by reference. International Application No. PCT/US2020/020143, claims benefit of U.S. Provisional Application No. 62/811,169, filed Feb. 27, 2019, the entirety of which is incorporated herein by reference.

BACKGROUND OF THE INVENTION

The nasal cavity, sinonasal cavity and nasopharynx are important components of the human respiratory system and can be affected by diseases or conditions requiring medical intervention. Proper and effective treatment of these diseases and conditions is necessary to promote the health of a patient and to avoid complications due to the disease or condition.

The current standard of care for diseases or conditions of these regions are saline nasal sprays or rinses, and corticosteroid, glucocorticoid, anticholergic, and antihistamine nasal sprays, which are generally low viscosity (1-10 cPs), water-based solutions or suspensions that are applied multiple times a day for an extended period of time. While steroidal nasal sprays address the inflammation resulting from the condition, it may not address the underlying cause if it is an infection. These at-home therapies also require a high level of patient compliance for efficacy. There are also currently no FDA approved antifungals for nasal administration. Thus, there is a need for an efficacious product topically administered to the sinonasal or nasopharyngeal tissue for antifungal therapy.

With respect to the underlying cause of the condition, in some instances a fungal and/or bacterial infection, the treatment involves irrigation of a water-based suspension of an antimicrobial or an antifungal in an in-clinic or hospital procedure that can include IV administration, and that may include anesthesia but most often are treated with nasal sprays at home by the patient, often in multiple daily doses. Alternatively or additionally, oral antibiotics and antifungals are prescribed. These treatments are often unsuccessful and patients continue to suffer from chronic infections and inflammation with no viable alternatives. Therefore, there is a need for a treatment option that addresses the deficiencies described above.

SUMMARY OF THE INVENTION

The present disclosure is directed to methods for treating diseases and conditions of the nasal, sinonasal and nasopharyngeal tissues.

In some embodiments, a method for treating a subject with a disease or condition associated with the nasal, sinonasal or nasopharyngeal tissues includes the step of administering a composition topically to the sinonasal or nasopharyngeal tissue of the subject, wherein the composition is a cream of high viscosity comprising a steroid and/or an agent with antimicrobial activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the present invention and the advantages thereof, reference is now made to the following description taken in conjunction with the accompanying drawings.

FIG. 1 is a bar graph representing the raw symptom severity scores for the 11 patients of Example 2 (F denoting female and M denoting male) with the blue bars representing the severity score prior to treatment and the red bars representing the severity score after treatment.

DETAILED DESCRIPTION OF THE INVENTION

Figure 2A:
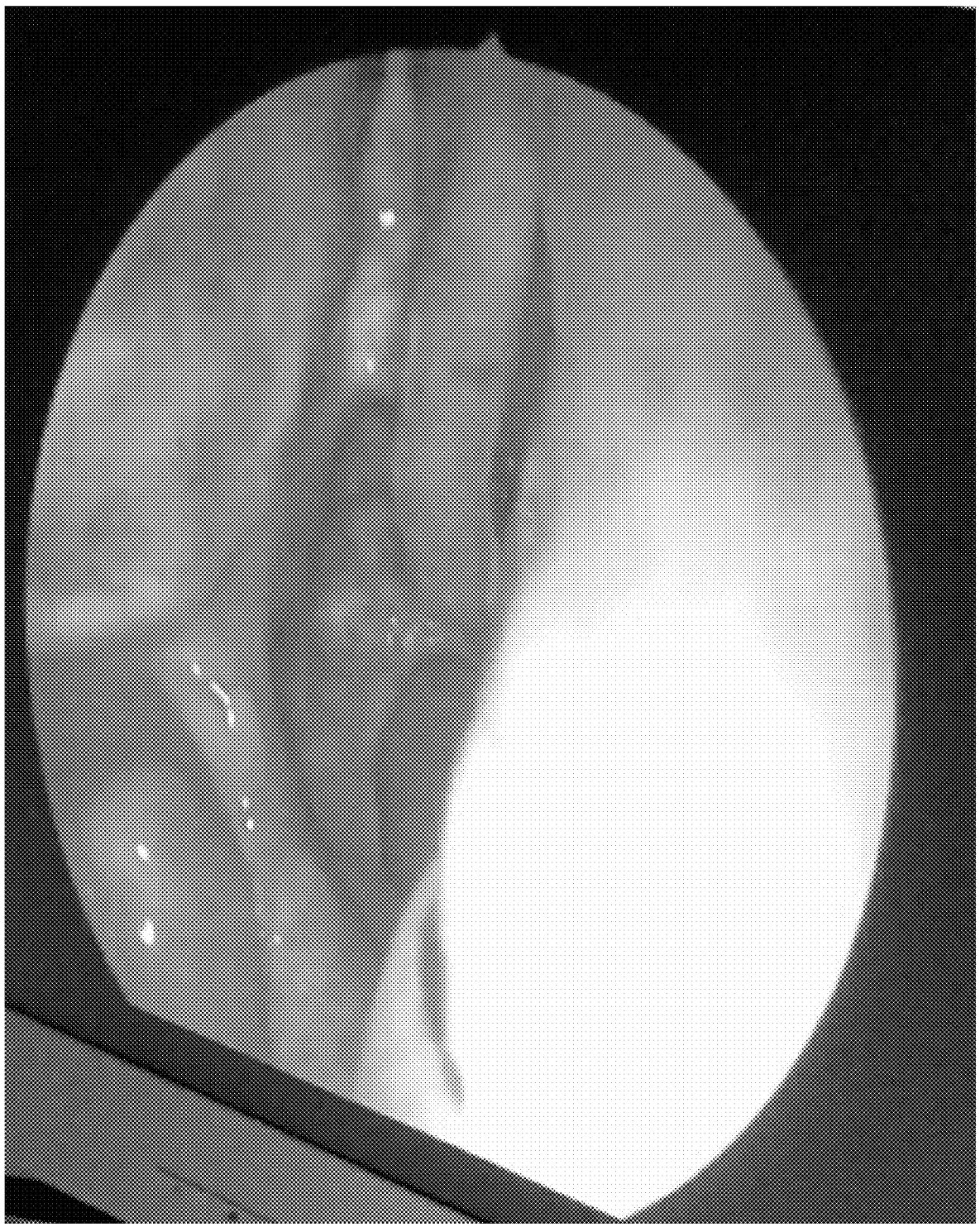
FIG. 2A represents an endoscopic photograph of the sinus of Patient 7 of Example 2 prior to treatment with the cream composition as described in Example 1.
Figure 2B:
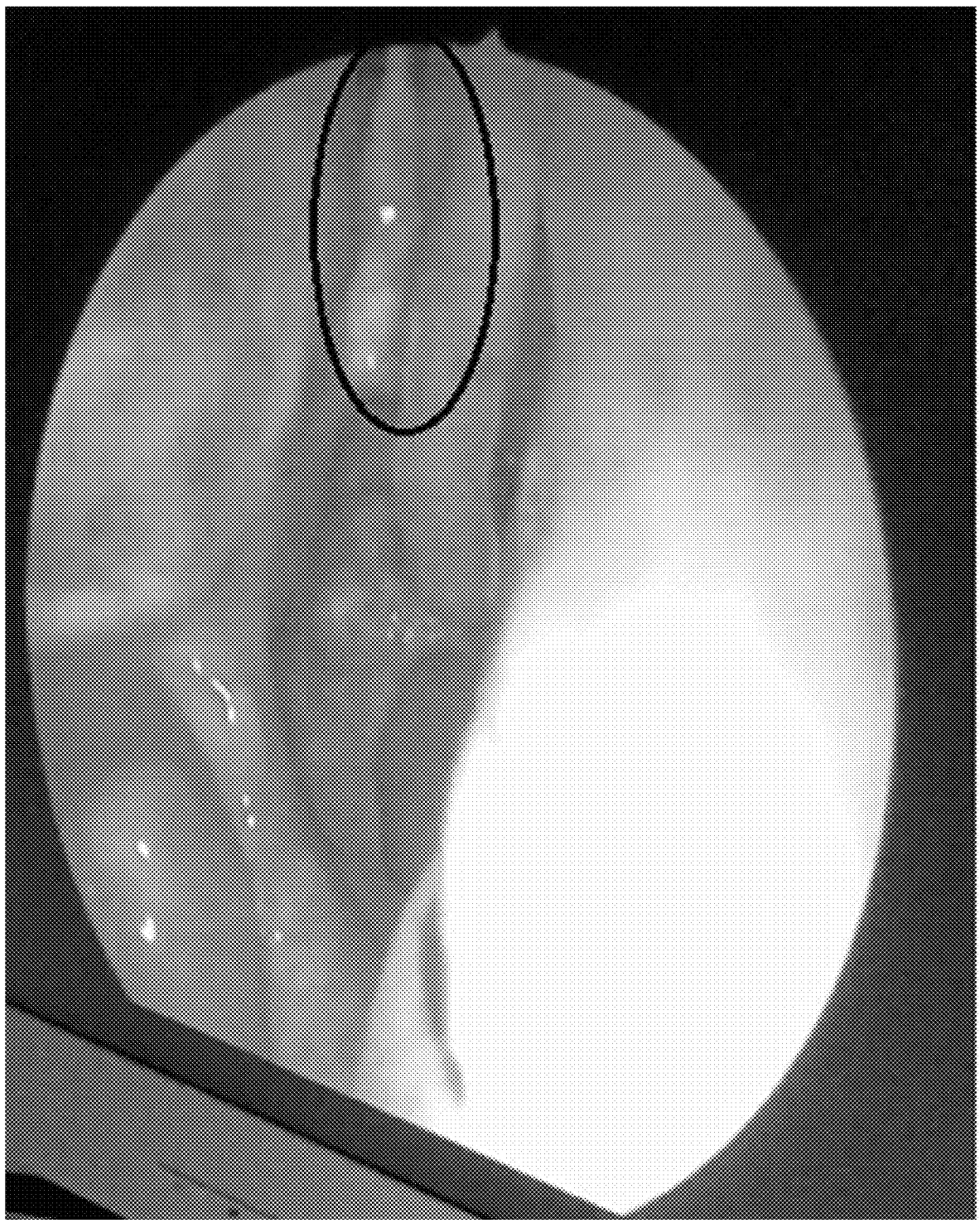
FIG. 2B represents an endoscopic photograph of the sinus of Patient 7 of Example 2 prior to treatment with the cream composition as described in Example 1 with the circled portion depicting mucus drainage.
Figure 2C:
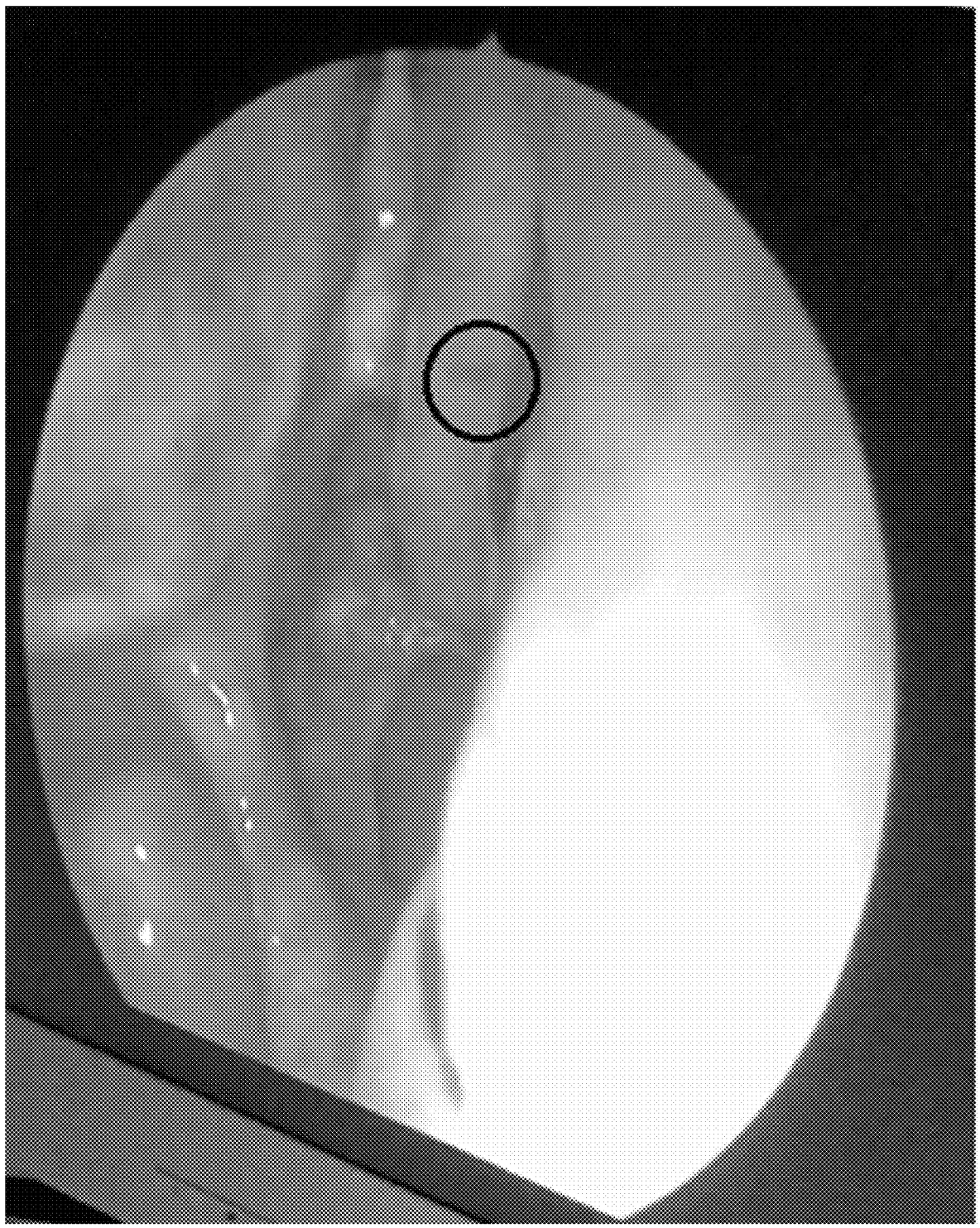
FIG. 2C represents an endoscopic photograph of the sinus of Patient 7 of Example 2 prior to treatment with the cream composition as described in Example 1 with the circled portion depicting hyperemia.

The present disclosure provides compositions and methods for treating diseases and conditions of the nasal, sinonasal and nasopharyngeal tissues.

Definitions

As used herein, the singular forms "a", "an" and "the" include plural referents unless the context clearly dictates otherwise.

The use of the term "or" in the claims and the present disclosure is used to mean "and/or" unless explicitly indicated to refer to alternatives only or the alternatives are mutually exclusive.

Use of the term "about", when used with a numerical value, is intended to include +/−10%. By way of example but not limitation, if a number of amino acids is identified as about 200, this would include 180 to 220 (plus or minus 10%).

As used herein, "antimicrobial" should be understood to include anti-microorganism such as antibacterial and antifungal.

As used herein, "effective amount" refers to an amount that is sufficient to bring about a desired pharmacologic and/or pharmacodynamic outcome. For example, an effective amount for treatment is an amount that can reduce or eliminate symptoms and/or the pathology of an infection or disease. Another example is an effective amount to disrupt or eradicate the biofilms protecting a pathogen to effectively eliminate it.

The terms "patient," "individual," and "subject" are used interchangeably herein, and refer to a mammalian subject to be treated, with human patients being preferred. In some cases, the methods of the invention find use in experimental animals, in veterinary application, and in the development of animal models for disease, including, but not limited to, rodents such as mice, rats, guinea pigs, and hamsters, as well as other animals including, but not limited to canines, felines, horses, and primates.

"Treatment" is an intervention performed with the intention of preventing the development or altering the pathology or symptoms of a disorder. Accordingly, "treatment" can refer to both therapeutic treatment and prophylactic or preventative measures. Those in need of treatment include those already with the disorder as well as those in which the disorder is to be prevented.

As used herein, the term "cream" means semisolid preparations containing one or more medicinal agents dissolved or dispersed in either an oil-in-water emulsion or water-in-oil emulsion. In avoidance of doubt, a "cream" does not include a "gel" which is a semisolid system consisting of dispersions of small or large molecules in an aqueous liquid vehicle rendered jelly like through addition of a gelling agent. Thus, the term "cream" does not include a thermoreversible gel, a thermoreversible polymer, or a copolymer of polyoxyethylene and polyoxypropylene.

In some embodiments, a method for treating a disease or condition of the nasal, sinonasal or nasopharyngeal tissues can include the step of administering a composition topically to the sinonasal or nasopharyngeal tissue of the subject, wherein the composition is a cream having a high viscosity comprising a steroid and/or an agent with antimicrobial activity.

In some embodiments, the step of applying the composition is performed as a single administration, which, in some instances, is sufficient to provide an effective treatment of a disease or condition of the nasal, sinonasal or nasopharyngeal tissues. In certain other embodiments, the step of applying the cream composition is performed only once per, by way of example but not limitation, every 10-21 days, every 21-30 days, every 30 to 60 days, every 60 to 90 days, every 90 days to 180 days, or every 180 days to 365 days. It should be understood that a "single administration" in most instances refers to sequential bilateral administration via intranasal administration. In some embodiments, the step of applying the cream composition is performed no more than twice per, by way of example but not limitation, 21, 30, 60, 90, 180, or 365 days.

In one embodiment, the step of administering the cream composition of the present disclosure comprises applying the cream composition via a first intranasal administration to the sinus mucosa. This initial application can be performed using a syringe having a tube or other like tool attached. The syringe having a tube or other like tool attached can be guided by a surgical endoscope. The method may then further comprise use of an instrument to spread the cream composition in a manner sufficient to cover the diseased sinus mucosa. These one or more steps can be repeated via a second intranasal administration to ensure bilateral coverage of the sinus cavity.

The amount of cream composition applied will vary based on extent of the size of the area of the diseased tissue and the size of the patient. In some embodiments, the composition can be administered in an amount of from about 0.5 cubic centimeters (cc) to about 5 cc per intranasal application or a total application amount to the diseased sinus tissue of from about 1 cc to about 10 cc, but more commonly from about 2 cc to about 4 cc per intranasal application or a total application amount to the diseased tissue of the sinus mucosa from about 4 cc to about 8 cc. By way of example, but not limitation, the amount of the composition administered per intranasal application can be about 0.5 cc, 0.75 cc, 1 cc, 1.25 cc, 1.5 cc, 1.75 cc, 2 cc, 2.25 cc, 2.5 cc, 2.75 cc, 3 cc, 3.25 cc, 3.5 cc, 3.75 cc, 4 cc, 4.5 cc, or 5 cc. It should be understood that for total bilateral application to the disease sinus mucosa, these recited amounts are doubled unless otherwise stated.

In other embodiments, the composition can be administered in an amount from about 0.5 grams (g) to about 5 g per intranasal administration or a total application amount to the diseased tissue of from about 1 g to about 10 g, but more commonly from about 2 g to about 4 g per intranasal administration or a total application amount to the diseased tissue of from about 4 g to about 8 g. By way of example, but not limitation, the amount of the composition can be about 0.5 g, 0.75 g, 1 g, 1.25 g, 1.5 g, 1.75 g, 2 g, 2.25 g, 2.5 g, 2.75 g, 3 g, 3.25 g, 3.5 g, 3.75 g, 4 g, 4.5 g, or 5 g per intranasal administration. It should be understood that for total bilateral application to the disease sinus mucosa, these recited amounts are doubled unless otherwise stated.

The compositions and methods of the present disclosure can be used to treat various conditions of the nasal, sinonasal, and nasopharyngeal tissues. By way of example, but not limitation, such conditions of the nasal, sinonasal and nasopharyngeal tissues can include disease, infections, symptoms and combinations thereof. By way of example but not limitation, such diseases or infections can include chronic sinusitis, acute sinusitis, mucormycosis, polymicrobic sinusitis, nasal polyps, bacterial sinusitis, allergic fungal sinusitis, chronic bacterial sinusitis, chronic allergic fungal sinusitis, and rhinosinusitis. By way of further example, but not limitation, methods of the present disclosure can be used for treating the following sinus symptoms: the need to blow the nose, nasal blockage, sneezing, runny nose, cough, post-nasal discharge, thick nasal discharge, ear fullness, dizziness, ear pain, facial pain or pressure, decreased sense of smell or taste, difficulty falling asleep, waking up at night, lack of a good night's sleep, waking up tired, fatigue, reduced productivity, reduced concentration, frustration, restlessness or irritability, sadness, embarrassment, and combinations thereof. In some embodiments, the condition further includes the need to blow the nose, nasal blockage, sneezing, runny nose, cough, post-nasal discharge, thick nasal discharge, ear fullness, dizziness, ear pain, facial pain or pressure, decreased sense of smell or taste, difficulty falling asleep, waking up at night, lack of a good night's sleep, waking up tired, fatigue, reduced productivity, reduced concentration, frustration, restlessness or irritability, sadness, embarrassment, or a combination thereof. Thus, these sinus symptoms can occur in conjunction with a disease, infection or other condition or can be conditions to be treated themselves. In some embodiments, a subject has previously undergone functional endoscopic sinus surgery (FESS) and thereafter developed a chronic inflammatory response. In some embodiments, a subject for which the present compositions and methods is useful is suffering from chronic allergic fungal sinusitis after FESS. In some embodiments, the patient is experiencing an exacerbation of symptoms after a period of mild or no symptoms after FESS with or without the use of nasal steroid sprays, oral antibiotics and/or nasal irrigations. In some embodiments, a subject has had FESS resulting in abnormal nasal tissue, described as hypertrophic, inflammatory, and granulation type tissue. In a further aspect of these embodiments, the subject's post-FESS sinusitis was treated with nasal steroid sprays, oral antibiotics and/or nasal irrigations for a period of a year with minimal to no change in disease state prior to performance of the present methods. In some embodiments, the subject is suffering from chronic sinus inflammation as a result of a bacterial infection. In some embodiments, the methods of the present disclosure can be performed at the time of FESS. In some embodiments, the patient has not previously undergone FESS. In some embodiments, the methods of the present disclosure can be performed during balloon sinus dilation. In some embodiments, the compositions of the present disclosure can be administered at the time of FESS. In some embodiments, the compositions of the present disclosure can be administered during balloon sinus dilation. Even in the instance the chronic inflammation is the result of a bacterial infection, cream compositions comprising clotrimazole may be useful as this active agent has been shown to have antibacterial activity in addition to its antimycotic activity against both gram-positive and gram-negative microorganisms. Specifically, clotrimazole has been shown to result in a reduction in *Pseudomonas aeruginosa* and to have antibacterial activity against Steptococci, Staphylococci, *Gardnerella vaginalis* and Corynebacteria. However, as discussed in further detail below, other antibiotic active agents can be substituted in the cream composition of the present disclosure. In some embodiments, the patient has no detectable microbial infection. In other embodiments, the patient has a detectable microbial infection, such as bacterial or fungal infection. Thus, the compositions and methods of the present disclosure can be useful in the absence or presence of detectable microbial infection. In some embodiments, the condition can include a bacterial infection. In some embodiments, the condition is at least partially the result of a bacterial infection and a biofilm has formed on the surface of the sinonasal or nasopharyngeal tissue. In some embodiments, the condition can include a fungal infection. In some embodiments, the condition can include a yeast infection. In some embodiments, the condition can include a polymicrobic infection.

The cream compositions of the present disclosure may comprise a steroid. Various corticosteroids, glucocorticoids or combinations thereof can be used in the compositions and methods of the present disclosure. By way of example but not limitation, corticosteroids that can be used in the compositions and methods of the present disclosure include cortisone, cortisol, hydrocortisone, methylprednisolone, prednisolone, prednisone, triamcinolone, betamethasone, ciclesonide, dexamethasone, 21-acetoxypregnenolone, alclometasone, algestone, amcinonide, beclomethasone, budesonide, chloroprednisone, clobetasol, clobetasone, clocortolone, cloprednol, corticosterone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednival, prednylidene, rimexolone, tixocortol, triamcinolone, triamcinolone acetonide, triamcinolone benetonide, triamcinolone hexacetonide, and the like. Esters, derivatives and salts, including hydrates and hydrogen chloride salts of corticosteroids can also be used in the compositions and methods of the present disclosure. For example, betamethasone is frequently administered as betamethasone dipropionate (which has the chemical name 9-Fluoro-11β,17,21-trihydroxy-16β-methylpregna-1,4-diene-3,20-dione 17,21-dipropionate, which has an empirical formula of $C_{28}H_{37}FO_7$, and which has a molecular weight of 504.59 g/mol), and the dosage given for betamethasone in Table 1 below is based on this particular salt.

The amount of steroid in compositions of the present disclosure can vary according to the desired dose to be delivered based on patient status, patient sensitivity, the biological half-life of the steroid, the patient's age, systemic factors and other factors. In addition, the state of the infection or disease and its susceptibility to the steroid can also be considered. One of skill in the art can determine an appropriate dosage, including determining an "effective amount" of the composition to apply.

Exemplary, non-limiting dosage ranges of specific steroids for use in the cream compositions of the present methods are shown below in Table 1. The values recited in Table 1 are for use in the current cream compositions and assumes a total single administration (i.e., bilateral intranasal administrations to the sinus mucosa) of cream composition of 5-6 grams (i.e., 2.5 to 3 g per intranasal administration).

TABLE 1

Exemplary, non-limiting dosage ranges for corticosteroids (in mg/g of composition)

| Steroid | Dosage Range | Preferred Dosage Range | More Preferred Dosage Range | Most Preferred Dosage Range | Biological Half Life (Hours) |
|---|---|---|---|---|---|
| cortisone | 20.8-104.2 | 41.7-83.3 | 45.8-72.9 | 52-62.5 | 8-12 |
| hydrocortisone | 16.7-83.3 | 33.3-66.7 | 36.7-58.3 | 41.6-50 | 8-12 |

TABLE 1-continued

Exemplary, non-limiting dosage ranges for corticosteroids
(in mg/g of composition)

| Steroid | Dosage Range | Preferred Dosage Range | More Preferred Dosage Range | Most Preferred Dosage Range | Biological Half Life (Hours) |
|---|---|---|---|---|---|
| Methyl-prednisolone | 3.3-16.7 | 6.7-13.3 | 7.3-11.7 | 8.3-10 | 18-36 |
| prednisolone | 4.2-20.8 | 8.3-16.7 | 9.2-14.6 | 10.4-12.5 | 18-36 |
| triamcinolone | 3.3-16.7 | 6.7-13.3 | 7.3-11.7 | 8.3-10 | 18-36 |
| Betamethasone (free steroid) | 0.5-2.5 | 1-2 | 1.1-1.75 | 1.25-1.5 | 36-54 |
| Betamethasone dipropionate | 0.643-3.215 | 1.286-2.572 | 1.5-2.0 | 1.60-1.929 | 36-54 |
| dexamethasone | 0.6-3.1 | 1.3-2.5 | 1.4-2.2 | 1.5-1.9 | 36-54 |

In some embodiments, the steroid is betamethasone or betamethasone dipropionate and is present in a composition of the present disclosure at from about 0.1 mg to about 0.5 mg per gram of cream composition or from about 0.15 to about 0.64 mg per gram of cream composition, respectively, or more preferably about 0.25 mg per gram of cream composition or about 0.32 mg per gram of cream composition, respectively. In another embodiment, the total dose of betamethasone dipropionate administered in a single application (i.e., bilateral intranasal administrations) is from about 0.643 mg to about 3.25 mg, or more preferably from about 0.80 mg to about 2.6 mg, or even more preferably from about 0.95 mg to about 1.93 mg, and even more preferably from about 1.28 mg to about 1.61 mg.

In some embodiments, the steroid is present at about 0.01 to about 1 weight percent of the composition. By way of example but not limitation, the steroid can be present at 0.01 to 0.5 weight percent of the composition, 0.02 to 0.4 weight percent of the composition, 0.03 to 0.3 weight percent of the composition, 0.04 to 0.2 weight percent of the composition, or 0.05 to 0.1 weight percent of the composition. In some embodiments, the steroid is betamethasone dipropionate and is present at about 0.03 weight percent of the composition.

Various antifungal agents can be used in the compositions and methods of the present disclosure. By way of example, but not limitation, such antifungal agents can include natamycin, ciclopirox, fluconazole, terbinafine, clotrimazole, ketoconazole, econazole, miconazole, nystatin, oxiconazole, terconazole, tolnaftate, efinaconazole, abafungin, terbinafine, butenafine, metronidazole and the like as well as combinations thereof. In some embodiments, the antifungal agent is clotrimazole.

The antifungal agent can be present in the compositions of the present disclosure at an effective amount. In certain embodiments, the effective amount or total amount of antifungal agent per single administration (i.e., bilateral intranasal administration) is from about 20 mg to about 50 mg and more preferably from about 25 mg to about 40 mg. In certain embodiments, the antifungal agent is in an amount of from about 2.5 mg per gram of cream composition to about 10 mg per gram of cream composition, and more preferably, about 5 mg per gram cream composition. In some embodiments, the antifungal agent is present at about 0.1 to about 5 weight percent of the composition. By way of example but not limitation, the antifungal agent can be present at 0.1 to 5 weight percent of the composition, 0.5 to 4 weight percent of the composition, 0.5 to 3 weight percent of the composition, 0.5 to 2 weight percent of the composition, 0.5 to 1 weight percent of the composition, 1 to 5 weight percent of the composition, 2 to 5 weight percent of the composition, 3 to 5 weight percent of the composition, 4 to 5 weight percent of the composition or about 0.1, 0.2, 0.3, 0.4, 0.5, 0.6, 0.7, 0.8, 0.9, 1.0, 1.5, 2.0, 2.5, 3.0, 3.5, 4.0, 4.5 or 5.0 weight percent of the compositions. In some embodiments, the antifungal agent is clotrimazole and is present at about 0.5 weight percent of the composition.

In some embodiments, a composition of the present disclosure can further comprise an antibiotic. By way of example, but not limitation, such antibacterial agents can include flucloxacillin, triclosan (2,4,4'-Trichloro-2'-hydroxydiphenyl ether), alcohols (including ethanol and isopropyl alcohol), peroxides (including benzoyl peroxide), iodine, benzethonium chloride, chloroxylenol and aminoglycoside antibiotics such as ciprofloxacin, and salts or derivatives thereof. By way of example but not limitation, other antibiotics can include amikacin, gentamicin, kanamycin, neomycin, netilmicin, streptomycin, tobramycin, paromycin, geldanamycin, herbimycin, loracarbef, ertapenem, doripenem, imipenem, meropenem, cefaclor, cefamandole, cefotoxin, cefprozil, cefuroxime, cefixime, cefdinir, cefditoren, cefpodoxime, ceftazidime, ceftibuten, ceftizoxime, ceftriaxone, cefepime, ceftobiprole, vancomycin, azithromycin, clarithromycin, dirithromycin, erythromycin, roxithromycin, troleandomycin, telithromycin, spectinomycin, aztreonam, amoxicillin, ampicillin, azociling, carbenicillin, cloxacillin, dicloxacillin, flucloxacillin, mezlocillin, meticillin, nafcillin, oxacillin, peperacillin, ticarcillin, bacitracin, colistin, polymyxin B, ciprofloxacin, clavulanic acid, enoxacin, gatifloxacin, levofloxacin, lomefloxacin, moxifloxacin, nonfloxacin, ofloxacin, trovafloxacin, grepafloxacin, sparfloxacin, AL-15469A, AL-38905, OP-145, mafenide, prontosil, sulfacetamide, sulfamethizole, sulfanilimide, sulfasalazine, sulfisoxazole, trimethoprim, cotrimoxazole, demeclocycline, doxycycline, minocycline, oxytetracycline, tetracycline, linezolid, arsogebanubem chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin, dalfopristin, rifampicin, thiamphenicol, tinidazole, amoxicillin/clavulanic acid, Maximin H5, Dermcidin, Cecropins, andropin, moricin, ceratotoxin, melittin, Magainin, dermaseptin, bombinin, brevinin-1, esculentins and buforin II, CAP18, LL37, abaecin, apidaecins, prophenin, indolicidin, brevinins, protegrin, tachyplesins, defensins, drosomycin, alamethicin, pexiganan or MSI-78, MSI-843, MSI-594, polyphemusin, colicin, pyocin, klebicin, subtilin, epidermin, herbicolacin, brevicin, halocin, agrocin, alveicin, carnocin, curvaticin, divercin, enterocin, enterolysin, erwiniocin, glycinecin, lactococin, lacticin, leucoccin, mesentericin, pediocin, plantaricin, sakacin, sulfolobicin, vibriocin, warnerinand, nisin, and the like, as well as salts or derivatives thereof.

The therapeutic active agents (steroids and/or antimicrobial agents) contemplated within the scope of the invention should be understood to include hydrophobic, hydrophilic and amphiphilic compounds. They may be in their free acid, free base, or pharmaceutically acceptable salt forms and include derivatives, esters or prodrugs. It should be understood that the cream compositions of the present disclosure may comprise only a steroid, only an antimicrobial agent (antifungal, antibacterial, or a combination thereof), or a combination of a steroid and an antimicrobial agent. The types of therapeutically active ingredients in the cream composition may be determined based on the condition treated and in some instances, may only require a steroid and in others only an antimicrobial agent, and in further instances both a steroid and an antimicrobial agent. Thus, in some embodiments, the cream composition does not include an antimicrobial agent. In other embodiments, the cream composition does not include a steroid. In such instances, by way of example, but not limitation, the cream composition can include only a steroid as a therapeutic active agent, i.e. the cream composition does not include an antimicrobial agent. In other instances, by way of example, but not limitation, the cream composition can include only an antimicrobial agent as a therapeutic agent, i.e. the cream composition does not include a steroid.

In some embodiments, the total amount of cream composition applied to the diseased region of the subject (i.e., bilateral intranasal administrations) is from about 4 grams to about 10 grams and more preferably from about 5 grams to about 8 grams. It should be understood therefore that the amount of cream composition administered per intranasal administration is from about 2 grams to about 5 grams and more preferably from about 2.5 grams to about 4 grams.

The compositions described herein are sufficiently viscous that they maintain contact with the tissues of the nasal, sinonasal, nasopharyngeal for a sufficient amount of time to provide effective treatment of those tissues.

It should be understood by one of ordinary skill in the art that the viscosity values of creams are largely dependent on the method by which viscosity is measured. Accordingly, the viscosity values of the cream compositions of the present disclosure are those generated by a Brookfield HBT with Spindle 21 at room temperature and comprises the following viscosity values under the corresponding recited conditions: (1) from about 220,000 centipoise (cP) to about 260,000 cP at a shear rate of 0.5 RPM, a % torque of 30 at a factor of 8000; (2) from about 140,000 cP to about 170,000 cP at a shear rate of 1.0 RPM, a % torque of 39 at a factor of 4000; (3) from about 75,000 cP to about 90,000 cP at a shear rate of 2.0 RPM, a % torque of 41 at a factor of 2000; (4) from about 55,000 cP to about 74,999 cP at a shear rate of 2.5 RPM, a % torque of 42 at a factor of 1600; (5) from about 32,000 cP to about 55,000 cP at a shear rate of 5.0 RPM, a % torque of 50 at a factor of 800; (6) from about 19,000 cP to about 32,000 cP at a shear rate of 10.0 RPM, a % torque of 60 at a factor of 400; (7) from about 10,000 cP to about 19,000 cP at a shear rate of 20.0 RPM, a % torque of 73 at a factor of 200; and (8) from about 5,000 cP to about 10,000 cP at a shear rate of 50.0 RPM, a % torque of 97 at a factor of 80 (collectively referred to herein as the "cream composition viscosity profile"). To avoid confusion, as used herein and in the amended claims, the term "cream composition viscosity profile" refers to the viscosity values recited above under the recited conditions using the Brookfield HBT with Spindle 21 at room temperature.

Various topical analgesics may also be used in the compositions described herein. These include, but are not limited to, nonsteroidal anti-inflammatory drugs, lidocaine, capsaicin, amitriptyline, glyceryl trinitrate, opioids, menthol, pimecrolimus, phenytoin and the like.

Various other materials may be used in the compositions described herein. These include, but are not limited to, astringents such as aluminum acetate, and topical anti-infectives such as neomycin, clioquinol, or chloramphenicol. By way of further example, but not limitation, the composition can further include any of cetostearyl alcohol, cetyl esters wax, sorbitan monostearate, benzyl alcohol, propylene glycol, 2-octyldodecanol, polysorbate 60, sodium hydroxide, carbomer 940 NF, water, and combinations thereof.

The pharmaceutical compositions described herein will preferably have a pH of less than about 7, since the use of compositions having higher pHs may promote, or inadequately discourage, the growth of bacteria and/or fungi in the target tissues. In some cases, the specific pH, or ranges of pH, prescribed for the pharmaceutical composition may depend on the particular corticosteroid, or combination of corticosteroids, chosen for the composition, since pH can have an effect on the solubility and/or shelf life of these materials.

The pharmaceutical compositions, and the methodologies for their application, will now be described with reference to the following non-limiting examples.

EXAMPLES

Example 1

A pharmaceutical composition in the form of a cream was prepared. The composition contained, as a first active ingredient, betamethasone dipropionate, a synthetic glucocorticosteroid which is an analog of prednisolone (betamethasone dipropionate is the 17,21-dipropionate ester of betamethasone). Betamethasone dipropionate has the empirical formula $C_{28}H_{37}FO_7$ and a molecular weight of 504.59 g/mol, and possesses the following structural formula:

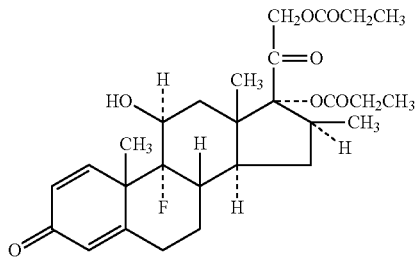

The cream composition further comprises a second active ingredient, clotrimazole, an antimicrobial agent. The cream composition further comprised various inactive ingredients as shown in Table 2 below which shows each active and inactive expressed as % wt based on the total weight of the cream composition.

TABLE 2

List of active and inactive ingredients by weight

| | % wt |
|---|---|
| Betamethasone Dipropionate | 0.0322 |
| Clotrimazole | 0.5000 |
| Cetostearyl Alcohol | 6.0000 |
| Cetyl Esters Wax | 1.5000 |
| Sorbitan Monostearate | 2.5000 |
| Benzyl Alcohol | 0.5000 |
| Propylene Glycol | 15.0000 |
| 2-Octyldodecanol | 6.7500 |
| Polysorbate 60 | 3.7500 |
| Sodium Hydroxide | QS* |
| Carbomer 940 NF | 0.5000 |
| Water | 62.9679 |

*"Quantity Sufficient" denotes that the material varies slightly as needed to adjust the pH.

The viscosity profile of the above cream composition was determined using a Brookfield HBT with Spindle 21 at room temperature which yielded the values below in Table 3 at the corresponding conditions.

TABLE 3

Viscosity testing results
Viscosity Testing
Brookfield HBT with Spindle 21

| RPM | % Torque | Factor | cP |
|---|---|---|---|
| 0.5 | 30 | 8000 | 240,000 |
| 1.0 | 39 | 4000 | 156,000 |
| 2.0 | 41 | 2000 | 82,000 |
| 2.5 | 42 | 1600 | 67,200 |
| 5 | 50 | 800 | 40,000 |
| 10 | 60 | 400 | 24,000 |
| 20 | 73 | 200 | 14,600 |
| 50 | 97 | 80 | 7,760 |
| 100 | Unreadable | 40 | — |

*All torque values taken after five full revolutions

The density of the above cream composition was determined to be 0.9 grams per cc.

The cream composition of this Example 1 was used in the following Example 2-5.

Example 2

This example demonstrates the efficacy of the cream composition described in Example 1 in 11 subjects (6 females and 5 males ranging in age from 17 to 72) who fit the following criteria:

1—Previous endoscopic sinus surgery over 1 year previous with minimum of maxillary antrostomies and ethmoidectomies.
2—Chronic severe nasal congestion and discharge unresolved with medical therapy including nasal irrigations.
3—Visual or CT indications of inflammatory and chronic disease.

The patients were treated by Dr. Patrick Slater at the Austin Ear Clinic in Austin, TX Prior to treatment, the symptom severity (congestion, fullness, and visual inspection of inflammation) was assessed by physician observation (inflammation) and having patients rate severity of congestion, fullness and drainage to yield a score on a scale of 1 to 10 with 10 being the most severe. The average severity score among the 11 patients was 8.62.

Patients were not sedated during treatment application, but were administered a topical spray application of lidocaine followed by pontocaine. The cream composition of Example 1 was then applied topically via bilateral intranasal administration to the sinus mucosa using an antrum suction tube attached to a syringe and then spread over the inflamed areas with a cue tip. The amount of cream composition applied was between 1.5 g and 4.5 g per intranasal administration for a total cream composition application of 3-9 g. Approximately 4 weeks following treatment, patients returned to the clinic for a follow-up visit to assess symptom severity according to the scale described above.

Figure 2D:
FIG. 2D represents an endoscopic photograph of the sinus of Patient 7 of Example 2 two months post-treatment with the cream composition as described in Example 1.
Figure 3A:
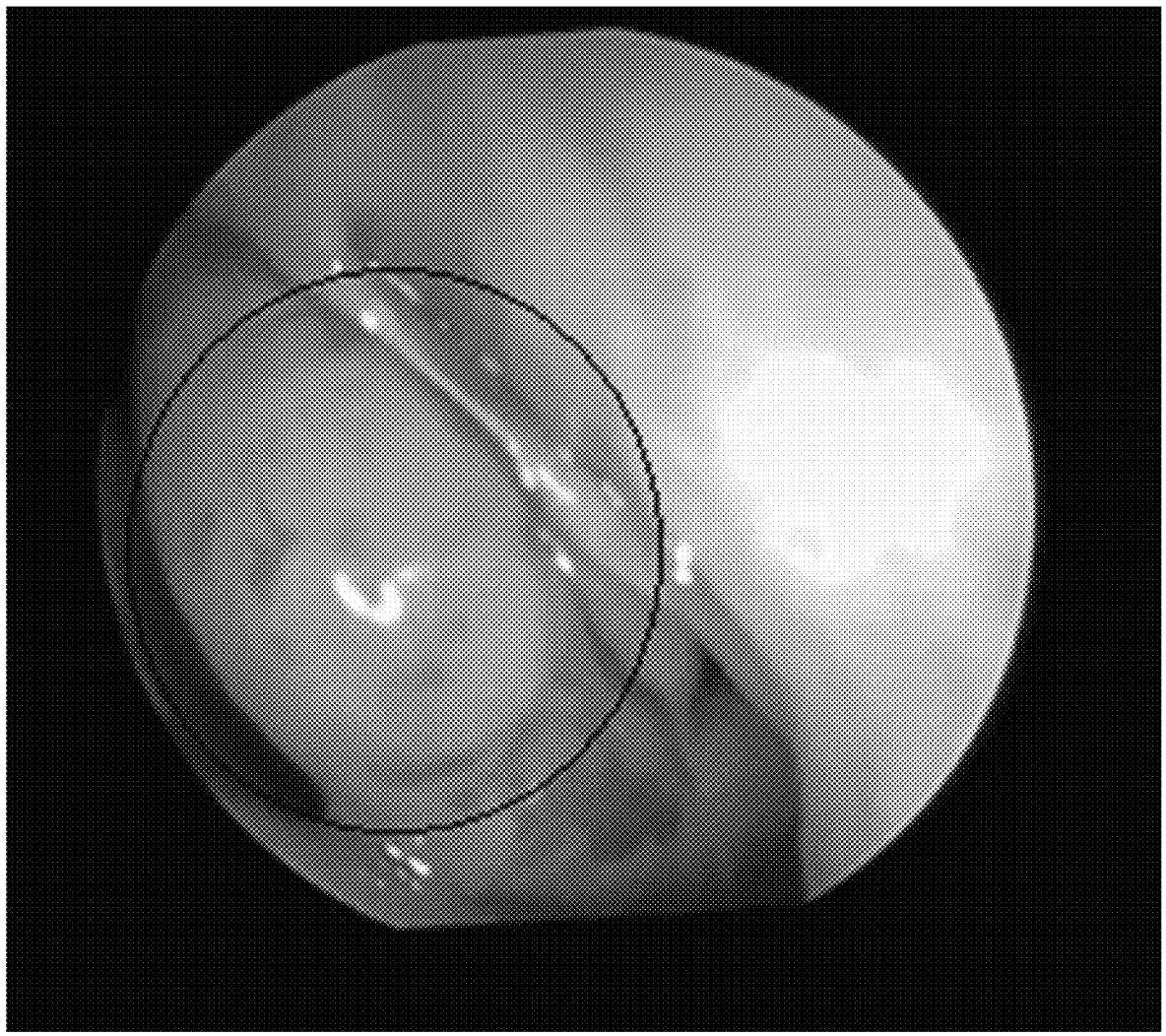
FIG. 3A represents an endoscopic photograph of the sinus of Patient 11 of Example 2 prior to treatment with the cream composition as described in Example 1.
Figure 3B:
FIG. 3B represents an endoscopic photograph of the sinus of Patient 11 of Example 2 two months post-treatment with the cream composition as described in Example 1.

Results: All 11 patients noted increase in congestion for the first 1-3 days post-treatment, but this resolved quickly with all patients noting significant improvement with congestion and drainage at about 4 weeks after initial application. The majority of patients reported that their breathability (lack of congestion), and drainage was at a level never experienced for many years. The average symptom severity improved to 2.53. Visual inspection after 2-6 months noted that the mucosa often returned to a normal appearance. The individual severity scores for each patient before and after treatment are shown in FIG. 1 where a severity score of 1 refers to normal sinus health. FIGS. 2A-2D provides pictures of the sinus mucosa in Patient 7 (from FIG. 1) before treatment (FIGS. 2A-2C) and 2 months post-treatment (FIG. 2D). As shown in FIG. 2D, Patient 7 displayed a complete resolution of inflammation (red mucosa shown in (FIGS. 2A-2C), mucus drainage (mucus circled in FIG. 2B), and a reduction in hyperemia (hyperemia circled in FIG. 2C). FIGS. 3A-3B provides pictures of the sinus mucosa in Patient 11 (from FIG. 1) before treatment (FIG. 3A) and 2 months post-treatment (FIG. 3B). Prior to treatment, FIG. 3A shows the left nasal cavity with the middle turbinate noted in the circle. The middle turbinate shows significant hyperemia, edema, granulation changes with minor bleeding. The area lateral to the middle turbinate shows polypoid changes and mild mucopurulence from the osteomeatal complex. Post treatment, FIG. 3B shows a reduction in all of the diseased changes noted prior to treatment most notably reduction in general inflammatory response highlighted by reduction in hyperemia, edema and granulation changes.

Figure 4A:
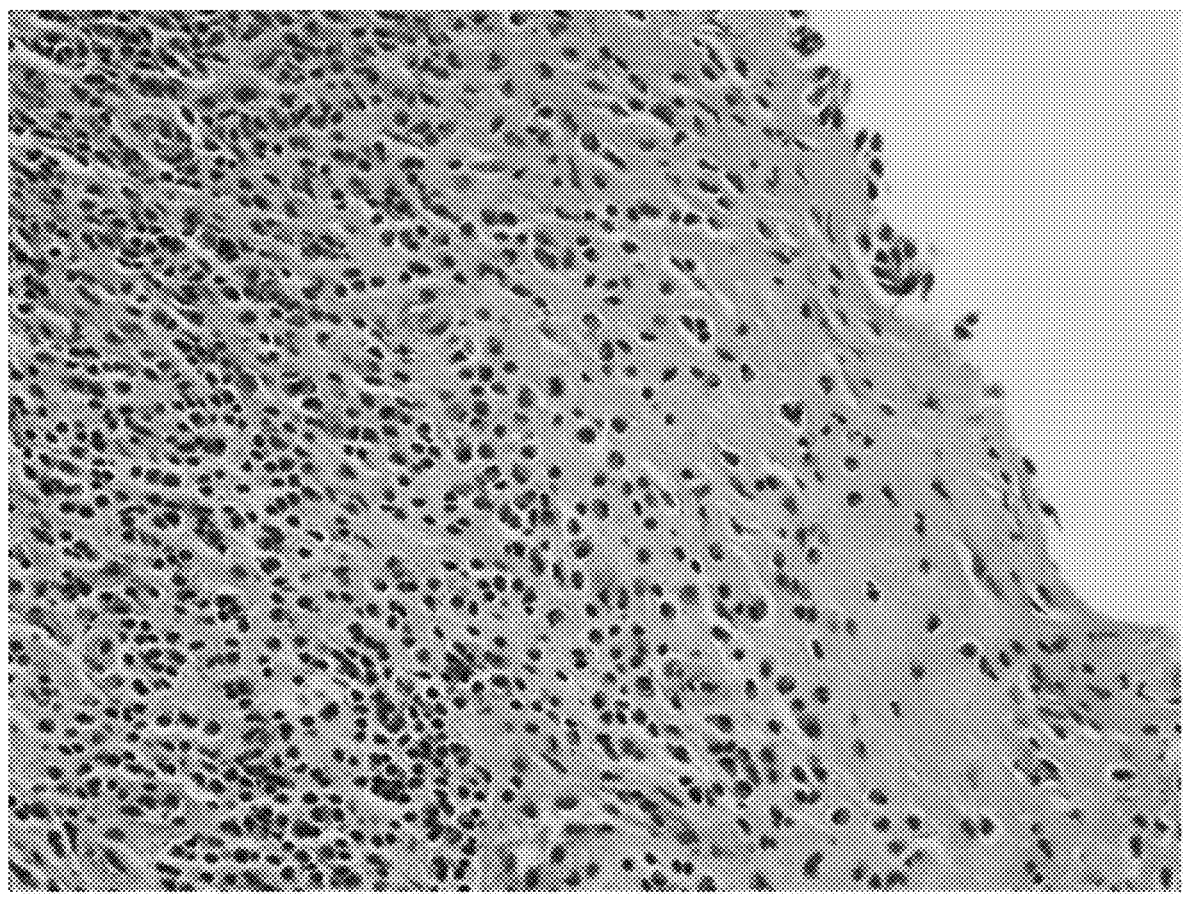
FIG. 4A represents a histology specimen taken from the lateral aspect of the middle turbinate of Patient 11 of Example 2 stained with haematoxylin and eosin just prior to initial application.
Figure 4B:
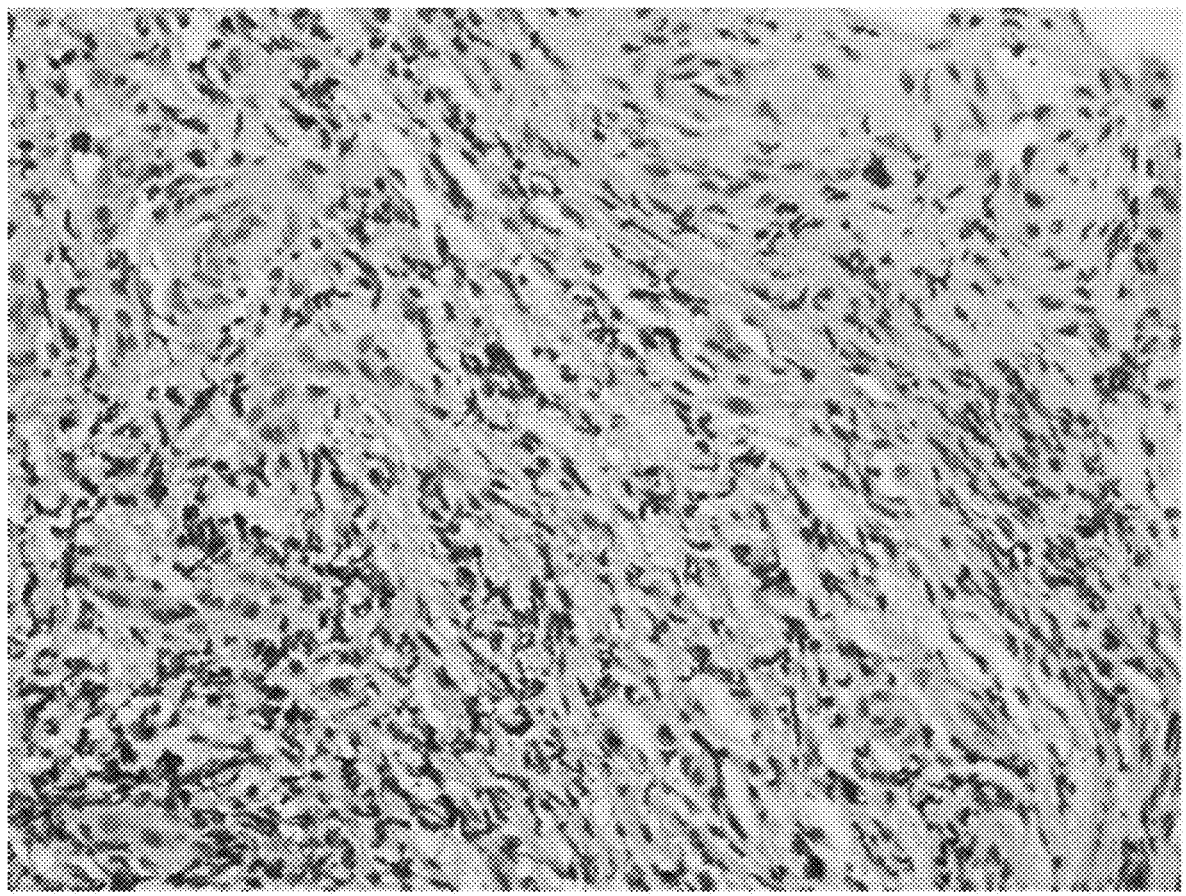
FIG. 4B represents a histology specimen taken from the lateral aspect of the middle turbinate of Patient 11 of Example 2 stained with haematoxylin and eosin at 2 months post initial application.

FIGS. 4A-4B provides a histology specimen taken from the lateral aspect of the middle turbinate of Patient 11 (from FIG. 1) just prior to initial application (FIG. 4A) and 2 months post-treatment (FIG. 4B). The biopsies were taken with a pair of cup forceps, stored in formalin and haematoxylin and eosin stained and photographed using high-powered magnification by a pathologist utilizing standard techniques. The tissue before treatment showed the significant presence of eosinophils (depicted in red) while the post-treatment tissue showed a significant reduction in the presence of eosinophils. It is believed, without being bound to theory, that a reduction in eosinophils can reduce sinus inflammation by reducing edema, thick mucus production and polyp formation that can be caused by inflammatory mediators released from eosinophils.

This Example demonstrates a substantially complete resolution of symptoms and inflammation which is rarely achieved by the previous standard medical therapies.

Example 3—Case Study

Patient History: A 59-year-old male patient presented with a history of bilateral sinus congestion, foul odor and shortness of breath for the past 3-4 months. The patient complained of a greenish yellow purulent discharge over last few months, along with sinus pressure. He had a history of recurrent sinus infections in the past 2 to 3 years. The patient had undergone FESS surgery around 19 years ago, which resulted in resolution of his sinus symptoms post-surgery. The symptoms started to return around 3 years ago and he has been on maximal allergy management since that time. The Patient graded his sinus congestion as 8 on severity scale described above in Example 2. He also reported an episode of a severe sinus infection and bronchitis about 2 months prior to visiting the clinic of Example 2 and was on a course of amoxicillin, under the care of the primary physician. He reported that congestion in the left nasal sinus, shortness of breath and purulent discharge had significantly increased since the infection.

Diagnosis: Endoscopic examination revealed mucin, mucosal inflammation and crusting. CT scan showed bilateral FESS surgery for maxillary sinuses, ethmoids, and frontal sinuses with mild mucosal thickening throughout. Cultures from the crusting's specimen grew *fusarium* species of fungi.

Treatment and Outcome: The cream composition of Example 1 was applied bilaterally as described in Example 2 to the ethmoids and maxillary antrostomy regions. Patient was instructed against nasal sprays for 2 to 3 days and called for a follow up visit after 2 weeks.

At the follow up visit, patient reported almost 50% improvement in his symptoms. Nasal odor, congestion and purulent discharge had reduced significantly and graded the severity of his symptoms as 4 based on the scale described in Example 2. Cream composition of Example 1 was reapplied to the ethmoids and maxillary antrostomy regions and was recalled after 2 weeks.

At the 2-week visit post second application, patient reported that the thick green-yellow purulent drainage had reduced by 80-90% and there was some clear and frothy drainage. There was no congestion present. Nasal microscopic exam was clear without any crusting or thick purulent mucin. Patient was recalled after 3 months.

Example 4—Case Study

Patient History: A 53-year-old female patient presented with the history of bilateral sinus congestion, ear and sinus pressure, difficulty in breathing, anosmia and constant thick mucus discharge from her nose. The severity of her symptoms had increased in the past year. She complained of severe facial pressure, fever, upper tooth ache, purulent discharge along with halitosis. The patient was treated using antibiotics in the past, but without any improvement in the symptoms. She has a history of multiple FESS surgeries (antrostomy, ethmoidectomy, sphenoidectomy) over the past 9 years for her chronic sinus issues. The patient was given a Medrol dose pack and a nebulizer, but she still felt starving for air.

Intranasal Examination and Diagnostic Imaging: Intranasal examination revealed mucosal inflammation, purulence and congested tissue with crust formation. The patient graded her sinus congestion as 9 on the severity scale described in Example 2. CT sinus was advised and showed chronic pan sinus disease with open ethmoidectomies and obstructed maxillary bilateral antrostomies.

Treatment: After informed consent, patient was placed in supine position. The nasal cavity was sprayed with tetracaine spray w/o epinephrine. Using an antrum suction tube attached to a syringe, the cream composition of Example 1 was applied to maxillary sinus mucosa, osteomeatal complex and nasal mucosa. Patient reported nasal fullness, pressure and congestion at the 24 hour follow up. The patient was recalled after 10 days for a follow up visit.

At the 10-day visit, the patient symptoms had regressed to 3 on the severity scale after the first application with reduction in active purulent drainage. Cream was reapplied and the patient was recalled in 4-weeks.

At the 4-week follow up, the patient demonstrated improvement of sinus congestion and drainage symptoms. The inflammation of the mucosa had resolved. She had mild facial pressure and upper tooth ache. Cream was reapplied in the maxillary sinus area. After 4 weeks following the third application, the patient reported resolution of her symptoms.

Example 5

This example further demonstrates the efficacy of the cream composition described in Example 1 in 8 subjects who fit the following inclusion criteria:
1. Male or nonpregnant, non-lactating female aged between 18 and 80 years
2. Able to understand and provide signed informed consent.
3. FESS within the past 20 years but no less than 6 months prior
4. Clinical diagnosis of exacerbation of sinusitis (suspected or confirmed due to bacteria, fungi, yeast, polymicrobic (bacteria, fungi and/or yeast)) with signs and symptoms such as congestion, discharge, inflammation of the nose and/or paranasal sinuses with current episode of >1-month duration. If bilateral sinus disease in present, both sinuses will be treated.
5. A score of at least 3 for congestion on a five-point scale (5 worse) (no minimum score for discharge is required).
6. Willing to submit to biopsy at Baseline and Exit Visits.
7. Willing to submit to CT imaging at Baseline and Exit Visits.
8. Willing to submit to microbiological sampling of affected sinus at Baseline and Exit Visits.
9. Willing to self-report sinus signs and symptoms daily (Appendix 2)
10. Females of childbearing potential must have a negative urine pregnancy test at screening and agree to use one of the following acceptable birth control methods:
    a. Surgically sterile (hysterectomy or bilateral oophorectomy)
    b. Surgically sterile (bilateral tubal ligation with surgery at least 6 weeks prior to study initiation)
    c. Intrauterine device (IUD) in place for at least 3 months
    d. Abstinence (not having sexual intercourse)
    e. Barrier method (condom or diaphragm) with spermicide for at least 14 days prior to screening and through study completion
    f. Stable hormonal contraceptive for at least 3 months prior to study and through study completion
11. Agree to refrain from water immersion of the sinuses during the conduct of the study
12. Patients who take analgesics or other non-steroid-containing maintenance medications (e.g., for arthritis) will be allowed in the study provided that the dose has been stable for at least 8 weeks prior to enrollment and must remain stable during the course of the study.
13. Normally active and otherwise judged in the opinion of the investigator to be in generally good health on the basis of medical history and physical examination.
14. Patients and/or caregiver(s) who are able to adhere to the visit schedule and protocol requirements and available to complete the entire study.

Patients were excluded who fulfilled any of the following criteria.
1. Females who are pregnant, breast feeding, or who wish to become pregnant during the study period
2. Signs and symptoms of current episode of sinusitis in the affected sinus(es) designated as "study sinus" of less than 1 month
3. History of diabetes mellitus, immune deficiency, allergy or intolerance to corticosteroids, oral steroid-dependent condition, clinical evidence of acute bacterial sinusitis, or clinical evidence of invasive fungal sinusitis.
4. History or diagnosis of glaucoma or ocular hypertension, presence of cataracts grade +3 or higher, or presence of posterior subcapsular cataract.
5. Clinically diagnosed sino-nasal disease other than exacerbation of sinusitis (e.g., congenital abnormalities of the sino-nasal area, obstructive bony exostosis or tumors, upper respiratory infections, including varicella and herpes simplex infections, cellulitis)
6. Glaucoma or cataracts of grade ≥2.
7. Known or suspected hypersensitivity to or allergy to clotrimazole, betamethasone dipropionate, or any other component of the study medication
8. Local sinus abnormalities such as abscess, or significant polyps in the affected sinus
9. Patient who is unwilling to discontinue use of nasal medications, rinse or spray for 3 days after investigational product application
10. Prior sinus surgery within 3 months of study entry in the affected sinus
11. Use of any systemic antibacterial medication within 2 weeks prior to enrollment
12. Patient with any type of device (e.g., PROPEL) in the nose or sinus
13. Surgical procedures in the nose or sinus after application of the investigational product for the duration of the study, unless prescribed by the PI after exiting the patient from the study
14. Previous enrollment in this study.
15. Oral steroids.
16. Systemic glucocorticosteroids other than inhaled asthma medications
17. Systemic or topical immunosuppressive drugs or immunomodulators (e.g., azathioprine, infliximab, calcineurin inhibitors).
18. Current enrollment in an investigational drug or device study or participation in such a study within 30 days of entry into this study.
19. Any significant medical or mental/psychiatric condition(s) which, in the PI's judgment, would interfere with the ability to provide informed consent or comply with study instructions, or that might confound the interpretation of the study results or put the patient at undue risk (this should include: Recent history of (within past 12 months), or strong potential for, alcohol or substance abuse.

Upon presentation with a diagnosis of post-FESS exacerbation of sinusitis lasting greater than 1-month, the patients were screened, examined and completed the Sino-Nasal Outcome Test (SNOT-22). The SNOT-22 provides an assessment of sinus health and is based on a scoring system of 0 to 5 (0=No Problem, 1=Very Mild Problem, 2=Mild or slight Problem, 3=Moderate Problem, 4=Severe Problem, 5=Problem as bad as it can be). The 22 metrics are:

1. Need to blow nose;
2. Nasal blockage;
3. Sneezing;
4. Runny nose;
5. Cough;
6. Post-nasal discharge;
7. Thick nasal discharge;
8. Ear fullness;
9. Dizziness;
10. Ear pain;
11. Facial pain/pressure;
12. Decrease Sense of Smell/Taste;
13. Difficulty falling asleep;
14. Wake up at night;
15. Lack of a good night's sleep;
16. Wake up tired;
17. Fatigue;
18. Reduced productivity;
19. Reduced concentration;
20. Frustrated/restless/irritable;
21. Sad; and
22. Embarrassed.

Microbiological specimens from the sinus were collected in addition to biopsy specimens before treatment and at the Exit Visit for assessment of eosinophil count for a subset of patients. Patients were then subjected to mechanical cleansing of the sinus by standard techniques, if indicated. The composition of Example 1 was then applied to the sinus(es) to be treated with a 4-inch flexible tip applicator attached to a syringe containing the composition of Example 1. 0.5 cc to 5 cc was administered per sinus.

30+/−7 days after the initial treatment, patients were assessed at an Exit Visit where a CT scan was obtained to assess the treated sinus(es), in addition to microbiological samples from the treated sinus(es) and biopsies from the maxillary ethmoid junction or lateral surface of the middle turbinate for a subset of patients. Patients also completed the SNOT-22 assessment at the Exit Visit. Exit Visits for Patients 4 and 5 were at 63 and 45 days post-treatment, respectively.

Patients received the following amounts of the composition:

| Patient No. | Amount of Drug applied, grams |
| --- | --- |
| 1 | 4.69 |
| 2 | 7.14 |
| 3 | 5.36 |
| 4 | 9.26 |
| 5 | 8.65 |
| 6 | 9.79 |
| 7 | 8.1 |
| 8 | 8.22 |

Figure 5A:
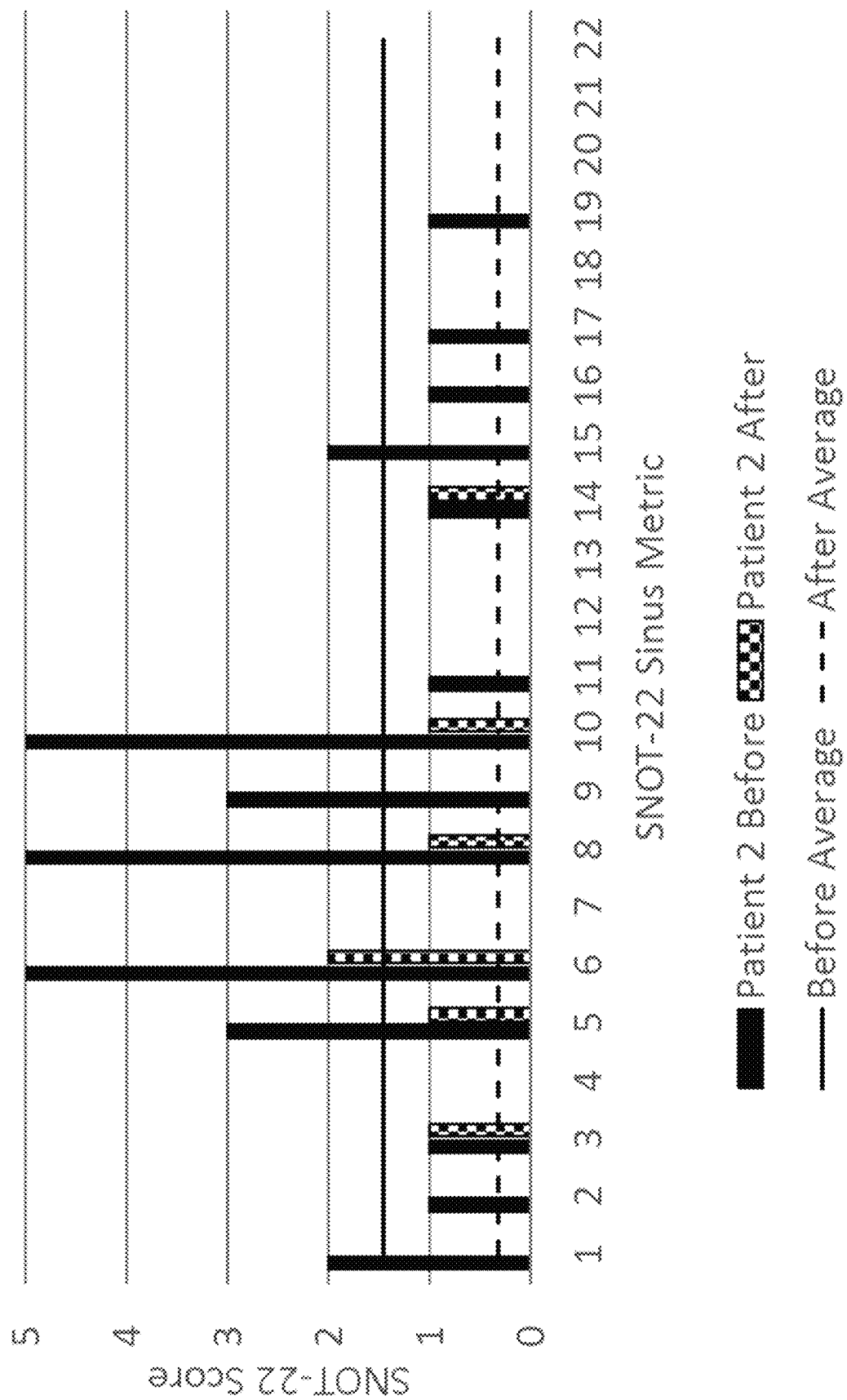
FIG. 5A represents the SNOT-22 scores for Patient 2 of Example 5 before and after treatment.
Figure 5B:
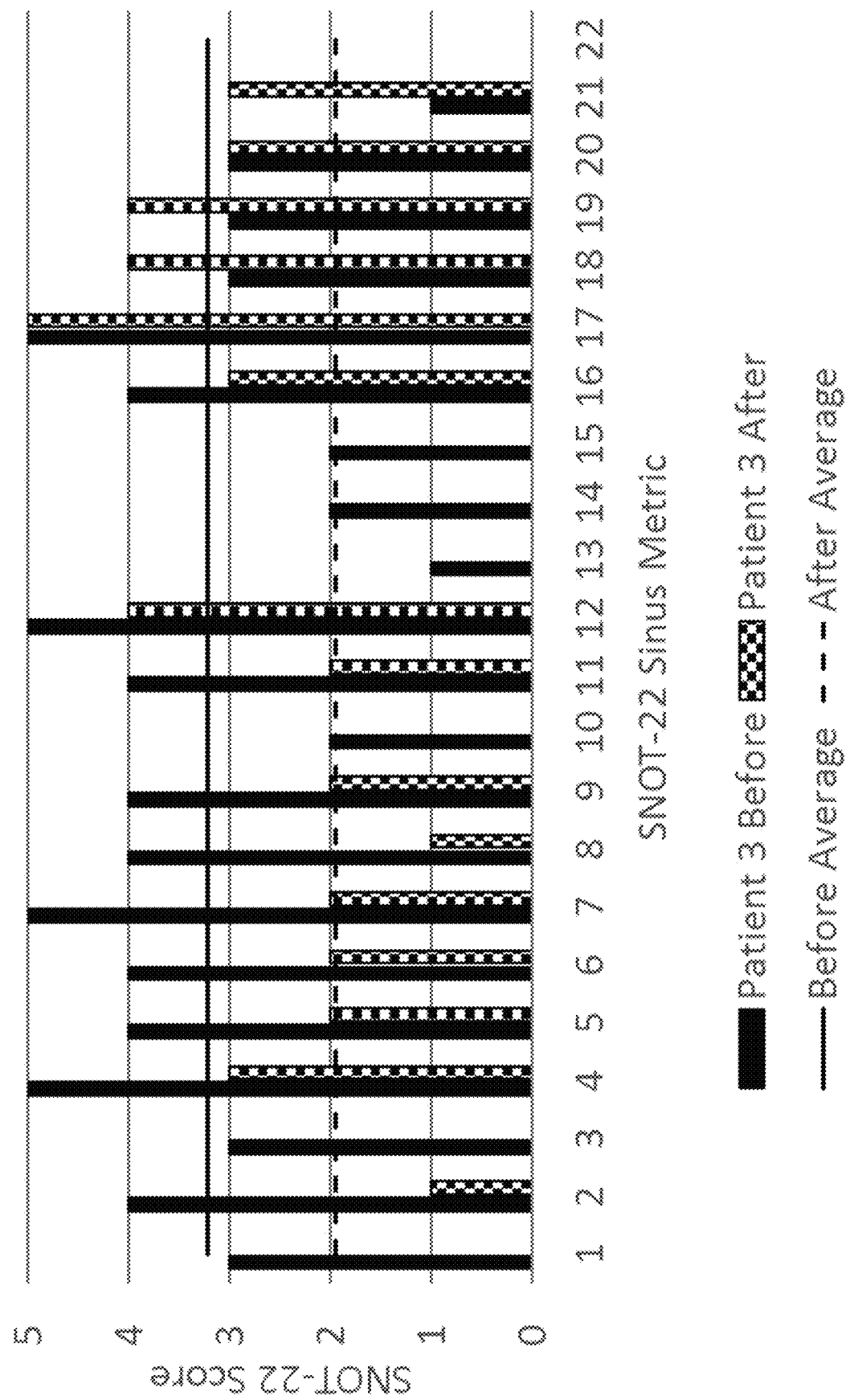
FIG. 5B represents the SNOT-22 scores for Patient 3 of Example 5 before and after treatment.
Figure 5C:
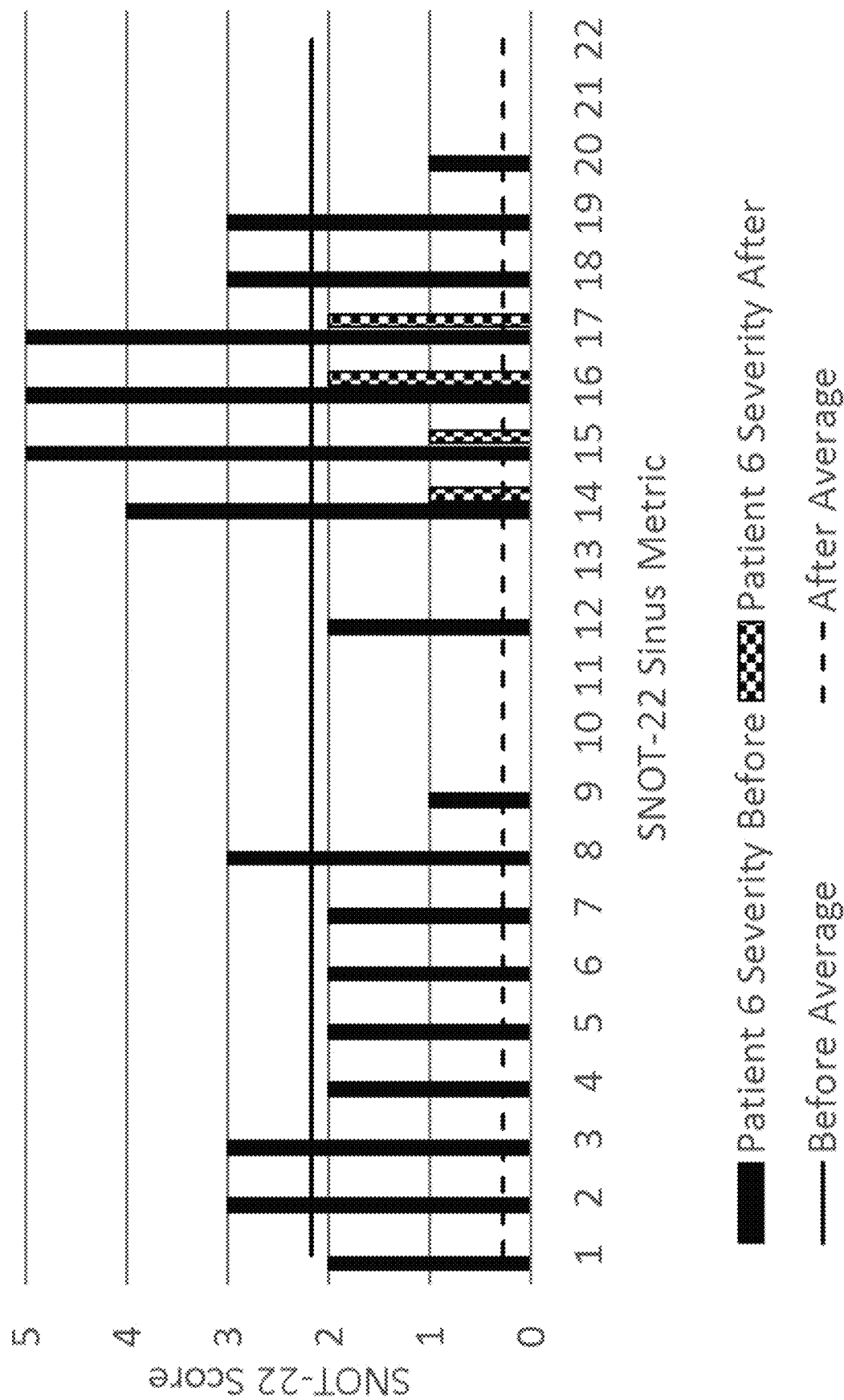
FIG. 5C represents the SNOT-22 scores for Patient 6 of Example 5 before and after treatment.
Figure 5D:
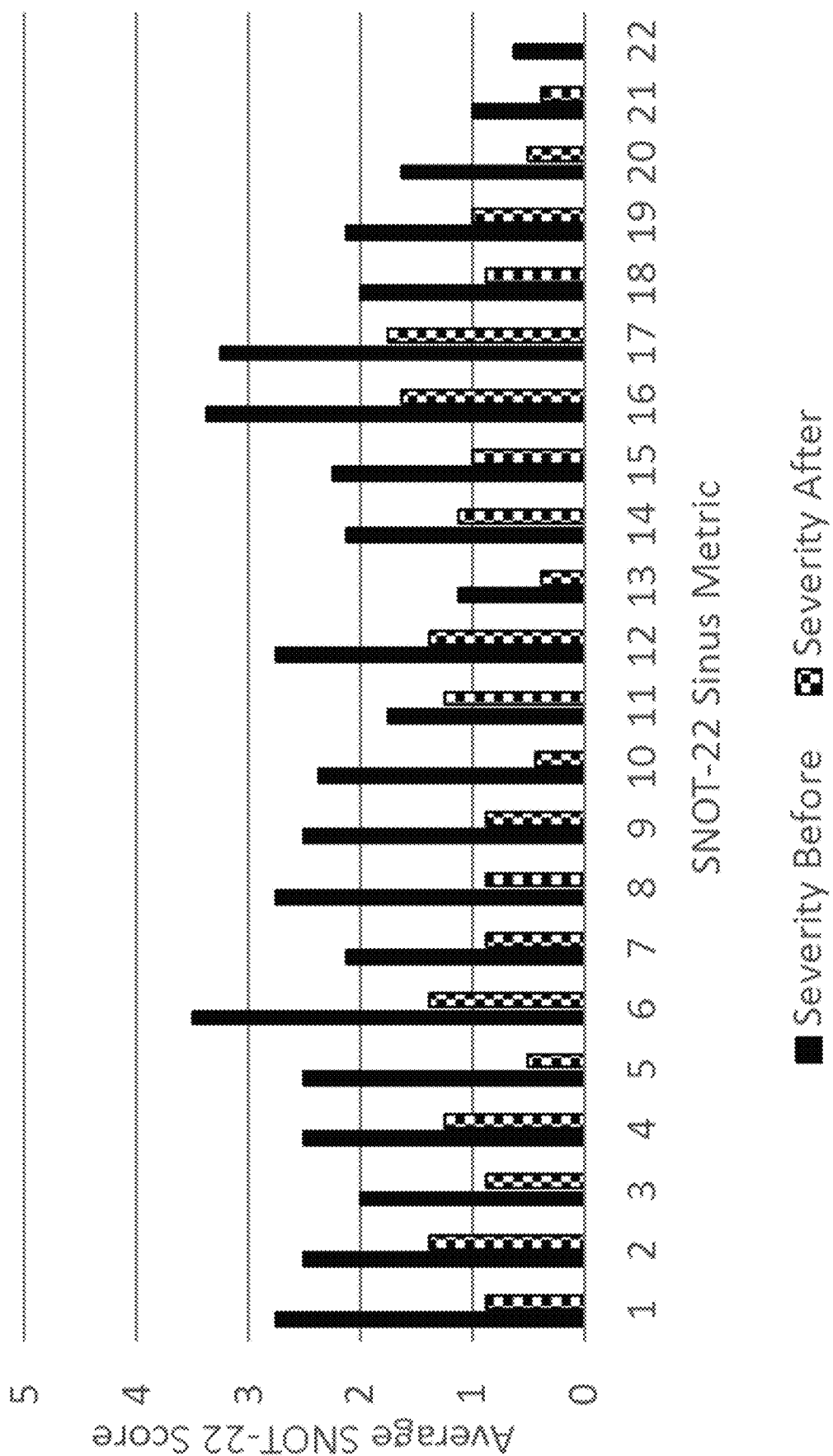
FIG. 5D represents the average SNOT-22 scores for each SNOT-22 metric for Patients 1-8 in Example 5, before and after (~30 days) treatment.

The SNOT-22 results for Patients 2, 3 and 6 are provided in FIGS. 5A-5C, respectively. Patient 2 was evaluated at 29 days post-treatment, Patient 3 was evaluated at 35 days post-treatment and Patient 6 was evaluated at 27 days post-treatment. At baseline, Patient 2 tested positive for 2+*Pseudomonas aeruginosa* (Mucoid strain) and 2+*Pseudomonas aeruginosa* (Non-Mucoid Strain) as well as 1+Dematiaceous fungus. At baseline, Patient 3 tested positive for 1+*Staphylococcus aureus*. At baseline, Patient 6 did not have a detectable bacterial or fungal infection. One patient (Patient 1) was found not to fulfill the study criteria after the initiation of the study, this patient indicated that their sinus symptoms were well controlled with nasal sprays. Average results for each SNOT-22 metric, before and ~30 days after treatment are shown in FIG. 5D.

Figure 6:
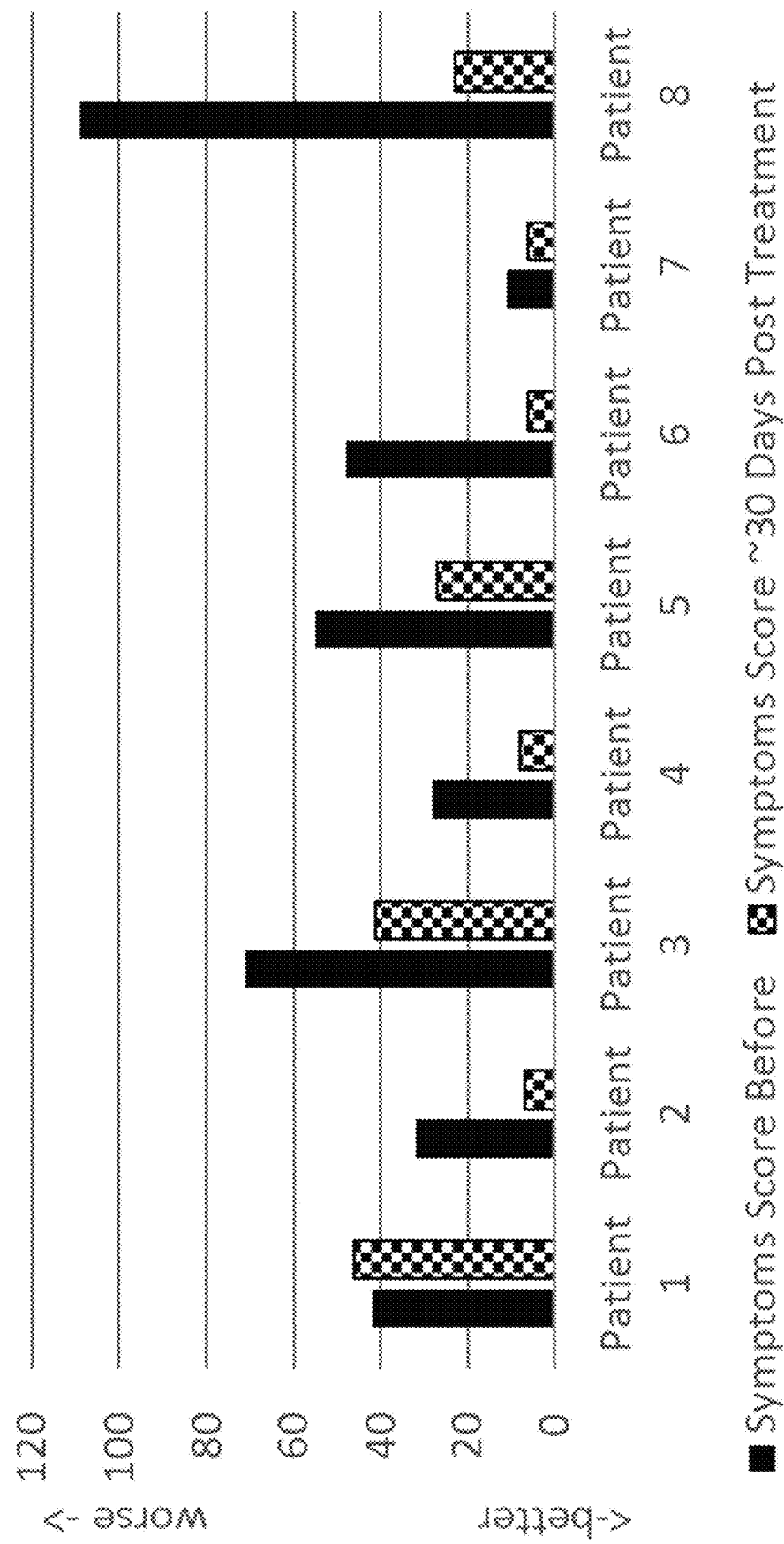
FIG. 6 represents the total SNOT-22 scores for patients in Example 5 before and after treatment.

As demonstrated in these figures, the composition was effective in improving the patients' sinus health as evidenced by a decrease in the overall average SNOT-22 score and by significant reductions in most of the 22 sinus health metrics. FIG. 6 provides a summary of the overall SNOT-22 scores for Patients 1-8 before and after treatment and likewise demonstrates the efficacy of the treatment by a significant reduction in the total SNOT-22 scores for the qualified patients (Patients 2-8).

Example 6—Case Study

A female aged 39 years old reported 10 sinus infections over the last year. She had 4 previous years of very similar circumstances and had been on multiple rounds of oral antibiotics including Bactrim and erythromycin. She has been on constant nasal steroids, and nasal antihistamine sprays. She has not had surgery on her sinuses.

She was scheduled for standard nasal endoscopic sinus surgery in two years prior but a move to Texas cancelled the procedure. Her symptoms over the years also include intense sinus pressure in frontal and maxillary region. Previous CT scan showed pan sinus disease of significant 4+mm mucosal changes, with mucopurulent drainage from her sinus ostea bilateral noted on physical exam.

Bilateral 6 sinus Balloon sinuplasty was performed approximately two years prior. Nasal symptoms and recurrent sinus infection completely resolved with elimination of her nasal congestion and drainage. This "normal status" persisted without any evidence of infection for approximately one year. Then for several months, she had a chronic sinus infection with facial pressure, pain, drainage, and mucopurulent discharge. These persisted for several months without resolution including antibiotic therapy. CT showed bilateral maxillary and frontal disease however reduced from previous CT scan that was performed prior to balloon sinuplasty.

Recently she underwent an application of the Betamethasone/Clotrimazole cream of Example 1 to the osteomeatal complex (OMC) bilateral under local anesthesia in the office, approximately 2 cc of ointment was placed in each OMC region. She was not placed on antibiotics after OMC application and on follow up about 5 days after application she had complete resolution of all symptoms including fullness, pressure, pain, congestion, drainage, and basically all of the above sinus complaints. Prior to treatment, the patient had reported her symptoms to be 7-8 out of 10 for congestion and drainage and 1 out of 10 for both after treatment.

She is back on her baseline medication for her nasal symptoms with nasal sprays and antihistamines. The latest evaluation showed she is stable with complete resolution of the nasal drainage, facial pain, nasal congestion and rhinorrhea.

All references, including publications, patent applications, and patents, cited herein are hereby incorporated by reference to the same extent as if each reference were individually and specifically indicated to be incorporated by reference and were set forth in its entirety herein.

The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating a subject with a condition associated with a sinonasal or nasopharyngeal tissue comprising administering a composition topically to the sinonasal or nasopharyngeal tissue of the subject, wherein the composition is a cream having a viscosity as measured by a Brookfield HBT with Spindle 21 at room temperature of (1) from about 220,000 centipoise (cP) to about 260,000 cP at a shear rate of about 0.5 RPM, a % torque of 30 at a factor of 8,000, (2) from about 140,000 cP to about 170,000 cP at a shear rate of about 1.0 RPM, a % torque of 39 at a factor of 4,000, (3) from about 75,000 cP to about 90,000 cP at a shear rate of about 2.0 RPM, a % torque of 41 at a factor of 2,000, (4) from about 55,000 cP to about 74,999 cP at a shear rate of about 2.5 RPM, a % torque of 42 at a factor of 1,600, (5) from about 32,000 cP to about 55,000 cP at a shear rate of about 5.0 RPM, a % torque of 50 at a factor of 800, (6) from about 19,000 cP to about 32,000 cP at a shear rate of about 10.0 RPM, a % torque of 60 at a factor of 400, (7) from about 10,000 cP to about 19,000 cP at a shear rate of about 20.0 RPM, a % torque of 73 at a factor of 200, or (8) from about 5,000 cP to about 10,000 cP at a shear rate of about 50.0 RPM, a % torque of 97 at a factor of 80, and wherein the cream further comprises a steroid.

2. The method of claim 1, wherein said steroid is selected from cortisone, cortisol, hydrocortisone, methylprednisolone, prednisolone, prednisone, triamcinolone, betamethasone, ciclesonide, dexamethasone, esters, derivatives and salts thereof, and combinations thereof.

3. The method of claim 1, wherein said steroid is betamethasone or an ester, derivative or salt thereof.

4. The method of claim 1, wherein said steroid is betamethasone dipropionate.

5. The method of claim 1, wherein said steroid is present in said composition at about 0.1 to 100 milligrams per gram of the composition.

6. The method of claim 4, wherein said steroid is present at about 0.322 milligrams per gram of the composition.

7. The method of claim 6, wherein the total amount of composition administered to the patient is from about 1 gram to about 10 grams.

8. The method of claim 1, wherein said disease or infection of the sinonasal or nasopharyngeal tissues is selected from mucormycosis, chronic sinusitis, acute sinusitis, bacterial sinusitis, chronic bacterial sinusitis, polymicrobic sinusitis, nasal polyps, allergic fungal sinusitis, chronic allergic fungal sinusitis, and rhinosinusitis.

9. The method of claim 1, wherein said subject has undergone sinonasal surgery prior to applying said composition.

10. The method of claim 1, wherein said disease or infection is chronic allergic fungal sinusitis, and wherein said subject has undergone functional endoscopic sinus surgery prior to applying said composition.

11. The method of claim 1, wherein the step of administering is performed not more than one time on the subject.

12. The method of claim 1, wherein the step of administering is performed not more than once in a 10 day period.

13. The method of claim 1, wherein the step of administering is performed not more than once in a 21 day period.

14. The method of claim 1, wherein the step of administering is performed not more than once in a 30 day period.

15. The method of claim 1, wherein the step of administering is performed not more than once in a 60 day period.

16. The method of claim 1, wherein the step of administering is performed not more than once in a 90 day period.

17. The method of claim 1, wherein the step of administering is performed not more than once in a 180 day period.

18. The method of claim 1, wherein the step of administering is performed not more than once in a 365 day period.

* * * * *